United States Patent [19]

Foker

[11] Patent Number: 4,605,644

[45] Date of Patent: Aug. 12, 1986

[54] METHOD FOR STIMULATING RECOVERY FROM ISCHEMIA EMPLOYING RIBOSE AND ADENINE

[75] Inventor: John E. Foker, Minneapolis, Minn.

[73] Assignee: Regents of the University of Minnesota, Minneapolis, Minn.

[21] Appl. No.: 699,037

[22] Filed: Feb. 7, 1985

[51] Int. Cl.$^4$ ............................................. A61K 31/70
[52] U.S. Cl. ........................................ 514/45; 514/23
[58] Field of Search ............................ 514/45; 536/23

[56] References Cited

PUBLICATIONS

H. G. Zimmer et al., Pflugers Arch., 376, 223 (1978).
H. I. Seifart et al., Basic Res. Cardiol., 75, 57 (1980).
J. E. Folker, et al., J. Thorac, Cardiovasc. Surg., 80, 506 (1980).
H. G. Zimmer, Science, 250, 81 (1983).
M. K. Pasque, et al., in J. Thorac, Cardiovasc. Surg., 83, 390 (1982).

*Primary Examiner*—Johnnie R. Brown
*Assistant Examiner*—Elli Peselev
*Attorney, Agent, or Firm*—Merchant, Gould, Smith, Edell, Welter & Schmidt

[57] ABSTRACT

The perfusion of ischemic tissue with dilute physiological salt solutions containing adenine and ribose reduces the period required for tissue function recovery and for the restoration of tissue of ATP levels.

7 Claims, No Drawings

METHOD FOR STIMULATING RECOVERY FROM ISCHEMIA EMPLOYING RIBOSE AND ADENINE

This invention was made with the assistance of a grant from The American Heart Association, Minnesota Affiliate, Inc. and grant numbers HL26640 and HL22152, awarded by the National Institutes of Health. The government has certain rights in this invention.

BACKGROUND OF THE INVENTION

Much of the increased safety of heart surgery has come from improved surgical techniques which can be used when the heart is still and quiet. A quiet heart is usually produced by cooling and depriving it of its blood supply. In addition, a cardioplegic solution is frequently injected into the vessels of the heart to produce cardiac standstill. Although these techniques have allowed enormous strides in cardiac surgery, there is still a price to be paid for this period of ischemia. The result is a period of depressed function (low cardiac output) following the operation which may or may not be reversible. Moreover, even if reversed for the short term, there is evidence that scarring can occur and later failure can result. Failure of recovery from ischemia due to myocardial infarctions or open heart surgery accounts for about 500,000 deaths per year in the United States.

As in other tissues, myocardial cell function and integrity require adenosine triphosphate (ATP) as the primary energy source. It is well known that both myocardial ATP levels and function are severly depressed by ischemia, and the recovery of cardiac energy metabolism after a period of ischemia has been widely investigated. Several important points have been established: (1) ATP levels do not rebound quickly with blood reperfusion, (2) the failure of this recovery is not due to impaired mitochondrial function because creatine phosphate levels rebound quickly to pre-ischemic values with reperfusion and cellular oxygen consumption is normal and (3) the factor that appears to limit most ATP regeneration is the enzymatic degradation and cellular leakage of ATP precursors.

During ischemic insult of a tissue, with concomitant hypoxia, the cellular energy reservoir of ATP is hydrolyzed first to adenosine diphosphate (ADP), then to adenosine monophosphate (AMP), adenosine (Ad) and finally adenine (A). Following reperfusion of blood, the energetic recovery via the synthesis of high energy ATP bonds in the cell is limited because of loss of these ATP precursors. Adenosine and adenine leak out of the cells, and adenine is further catabolized to end products and cannot reenter the cycle. Endogenous synthesis of ATP precursors through the purine biosynthetic pathway, the major normal route of synthesis, proceeds slowly, is metabolically demanding, and thus limits ATP recovery.

After a period of myocardial ischemia under the conditions of clinical open heart surgery, ATP levels require about ten days to fully recover. Myocardial function has been determined to require a similar period for full return. The most sensitive aspect of myocardial function was found to be the relaxation rather than the contraction phase of the heartbeat. It is the relaxation phase, or diastole, that requies almost ten days to return to normal. When relaxation ia incomplete, the heart does not fill satisfactorily and, therefore, less blood is ejected with each beat.

The theory that a reduction in the ATP recovery time could lead to improved cardiac function has lead to research aimed both at preventing the initial loss of ATP precursors from the cell and at methods for the resupply of the precursors employed in ATP biosynthesis.

Many investigators have attempted to show that precursor infusion will augment ATP recovery. Adenosine, adenine, inosine, 5-amino-4-imidazolcarboxamide riboside and ribose are some of the ATP precursors that have been marginally useful in increasing ATP regeneration after ischemia. Most studies were of short duration and only partial ATP recovery was found. Furthermore, precursors which are relatively distant in terms of the enzymatic steps required to reform ATP may be less efficient in inducing ATP recovery, while structurally more-closely related ATP precursors such as adenosine exhibit undesirable side-effects such as renal vasoconstriction or slowed atrioventricular conduction.

Therefore, the need exists for a method to improve the recovery of myocardial function after partial or total occlusion. A need also exists for a general method for the treatment of ischemic tissue to quickly restore normal ATP levels, both to improve tissue survival and to hasten general bodily recovery.

BRIEF DESCRIPTION OF THE INVENTION

The present invention provides a method for reducing the period of tissue function recovery following ischemic insult comprising perfusion of the tissue with a solution incorporating a mixture of adenine and a physiologically-acceptable pentose or pentitol, preferably ribose. This method shortens the period required for substantially complete recovery of ATP levels from about ten days to about 1–2 days. Furthermore, with respect to cardiac tissue, the return of heart function (diastole) closely parallels the return of ATP levels.

Adenine and ribose are infused in an amount effective both to restore and maintain the tissue ATP levels at a level substantially equal to that present in the preischemic tissue. Although it was expected that once an amount of adenine and ribose effective to restore the ATP level had been infused, the level would be maintained by the tissue, it was surprisingly observed that the effects of ischemia, and the accompanying net ATP catabolism are not immediately reversed by the restoration of ATP levels and tissue function. Thus, both ATP levels and cardiac function were observed to fall following premature cessation of the adenine-ribose infusion. Therefore, the present method also comprises continuing the infusion for the full duration of the ischemic effects, e.g., until the net catabolism of ATP has ceased, and not merely to the extent necessary to restore the tissue ATP levels.

Adenine/ribose infusion is a physiologically innocuous procedure. The only undesired effect is a tendency to lower blood sugar, a condition which is easily monitored and corrected. Therefore, the method of the present invention need not be limited to extreme situations such as those accompanying cardiac surgery, but can be extended to any situation in which hypoxia threatens tissue function.

DETAILED DESCRIPTION OF THE INVENTION

The present method comprises the perfusion of ischemic tissue such as myocardial tissue, with a solution comprising adenine (6-amino-purine) and a physiologically-acceptable pentose or pentitol. Pentoses which have been demonstrated to be effective to enhance adenine nucleotide biosynthesis in heart tissue models include d-(−)-ribose and d-(+)-xylose, and useful pentitoses include ribitol and xylital. See H. G. Zimmer et al., *Pflugers Arch.*, 376, 223 (1978), the disclosure of which is incorporated by reference herein. Of the pharmaceutically-acceptable pentoses, ribose is preferred for use with adenine in the practice of the present invention, and will be referred to hereinafter as the second component in the perfusion solutions, for the sake of brevity.

The adenine, or a pysiologically-acceptable salt thereof, and the ribose are dissolved to the desired concentration in an aqueous vehicle suitable for tissue perfusion. Preferred vehicles are those solutions commonly referred to as intravenous (IV) fluids. These fluids include aqueous solutions comprising amino acids, sugars such as dextrose, fructose and invert sugar, protein hydrolysates, sodium chloride, potassium chloride, calcium chloride, sodium lactate and mixtures thereof. Such commercially-available intravenous fluids, and methods for their infusion, are disclosed in *Remington's Pharmaceutical Sciences*, A. Osol, Ed., Mack Publishing Co. (16th ed.) at pages 1488-1497, the disclosure of which is incorporated by reference herein.

The infusion rate of the adenine-ribose mixture, the infusion period, and the total dose delivered can be varied over a wide range and will be dependent on a number of variables, including (a) the type of tissue perfused, (b) the extent of the ischemia, (c) the physical characteristics and condition of the subject and (d) the mode of administration of the infusion solution. Since the target tissue will commonly be treated by infusion of the adenine-ribose solution into the subject's bloodstream, the rate of administration of the perfusion solution can be readily adjusted. Widely-employed techniques, such as those employed for the infusion of IV solutions, can be utilized for introduction of the present solutions into the circulatory system, either by direct input into the circulatory system or via introduction into an extracorporeal stream of the blood. In the case of patients requiring immobilization of the heart, the present solutions can be infused directly into a chamber of the heart at or near the time that blood reperfusion is begun. An atrial infusion technique is fully set forth in the Examples.

Dilute solutions of adenine and ribose in normal (0.9%) saline were found effective to decrease the ATP recovery time following myocardial ischemia in the canine model. For example, infusion of a normal saline solution which is 20 mM in adenine and 80 mM in ribose at a rate of about 1 ml/min for about 24.0 hours afforded an eight-fold decrease in the ATP recovery time. During this treatment period, about 4.0 g of adenine and about 17.0 g of ribose were introduced into the circulatory system; a total dose of about 130-160 mg/kg of adenine and about 550-700 mg/kg of ribose. The appropriate dose for the optimal recovery of ATP levels and cardiac function in a given human subject can be readily established via empirical studies including known assays for ATP levels, cardiac function and energy level and the like.

The invention will be further described by reference to the follwoing detailed examples.

EXAMPLE 1

Recovery of the Working Canine Heart Following Global Myocardial Ischemia

A. Surgical Protocol

Sixteen conditioned dogs weighing 25 to 30 kg were anesthesized intravenously with thiopental (Sodium Pentothal) (12.5 mg/kg) and ventilated with a Harvard respirator with supplemental oxygen provided to maintain a $PaO_2$ of at least 100 mm Hg. Anesthesia was maintained with nitrous oxide and halothane. Temperatures were monitored continuously with an esophageal temperature probe (Electromedics, Englewood, Cal.). A right thoracotomy was performed through the fifth intercostal space and the aorta was cannulated through the internal mammary artery for arterial pressure monitoring and blood sampling. Blood pressures were measured with Statham P23Db strain gauges and recorded along with lead II ECG tracings on a Dynograph eight-channel recorder (Beckman Instruments, Inc., Schiller Park, Ill.). Blood gases were measured with a Model 326 Blood Gas Analyzer (Instrumentation Laboratory, Inc., Lexington, Mass.). Hemoglobin was measured with a Hemoglobinometer (Coulter Electronics Inc., Hialeah, Fla.). All instruments were calibrated at the beginning, middle, and end of each experiment. Silicone rubber catheters were placed in the left atrial appendage for pressure monitoring, the right atrial appendage for saline solution or drug infusion, and the coronary sinus for blood withdrawal. Catheter positions were confirmed at the completion of each study.

After anticoagulation with heparin (1250 $U \cdot kg^{-1}$), the animals were placed on total cardiopulmonary bypass (CPB) a normothermia (37° C.) according to standard techniques. The arterial perfusion was retrograde from the left femoral artery and the venous drainage from the superior and inferior venae cavae was via the right atrium. The axygos vein was ligated. The left ventricle was vented through the apex. Model S100A bubble oxygenators (Shiley, Inc., Irvine, Cal.) were used. Mean aortic pressure was maintained at 60 to 80 mm Hg by adjusting pump flow to approximately 100 $ml \cdot kg^{-1}$. min with a Biotronics electromagnetic flow transducer in the arterial infusion line.

B. Experimental Protocol

After beginning CPB, the dogs were allowed to stabilize for 5 to 10 minutes. Nearly simultaneous left ventricular transmural and septal biopsies were performed for measurement of adenine nucleotide levels. Global myocardial ischemia was then produced by cross-clamping the ascending aorta at normothermia (37° C.) with total arrest occurring within 5 to 7 minutes. The left ventricle was decompressed through the biopsy site. While the aorta was clamped a silicone rubber catheter with a Teflon felt sewing ring was sutured into the right ventricular free wall. After a 20-minute ischemic period, transmural and septal biopsies were repeated and the aortic cross-clamp was removed. Adenine (20 mM) and d-(−)-ribose (80 mM) in saline or saline (0.9%) infusion (1 ml/min) was started at the beginning of reperfusion via the righ atrial catheter. Defibrillation was accomplished with 5 to 10 W/sec of direct current after 20 minutes of reperfusion, and 10 minutes later the dogs were weaned from CPB and the heparin was reversed from protamine sulfate (50 to 100 mg). The dogs were supported for an additional 60 minutes off CPB, the biopsy cannula was brought through the lateral chest wall, and the chest incision was closed. During this time lactated Ringer's solution and/or whole blood was infused to maintain a left atrial pressure of 5 to 8 mm Hg and a hematocrit level of 30% to 40%.

The infusion of either adenine/ribose or saline solution into the right atrium was continued for 48 hours after the end of the ischemic period. Repeat septal biopsies were performed at 4 hours and 1, 2, 3, 5, and 7 days after ischemia. Biopsies were taken sequentially from the apex of the septum toward the base of the septum to avoid rebiopsy of the same area. Simultaneous aortic and coronary sinus blood sampls were obtained at 24 hours of infusion for determination of adenine levels.

C. Nucelotide and Nucleoside Assays.

Biopsies for adenine nucleotides and nucleosides were frozen within 1 second in liquid nitrogen-cooled 2-methylbutane. Blood samples were centrifuged and the plasma was mixed with equal parts of 2M perchloric acid. The tissue was extracted within 24 hours in 7.1% perchloric acid, homogenized, and centrifuged at $1000 \times g$. The supernatant was neutralized (pH 7.2) with 2N KOH, 0.4M imidazole, 0.4M KCl for myocardial biopsies, and saturated KOH for blood samples, centrifuged to remove potassium perchlorate, and stored at $-70°$ C. ATP, ADP and AMP were assayed by the methods set forth in *Methods of Enzymatic Analysis*, H. V. Bergmeyer, Ed., Academic Press (1974) at pages 1777-8 and 2126-29, respectively, the disclosure of which is incorporated by reference herein.

Purine nucleoside levels were determined by the method of H. K. Webster, et al., *J. Chromatography*, Vol. 209, 283-292 (1981), the disclosure of which is incorporated by reference herein.

D. Reagents, Calculations and Statistical Analyses

Reagents. High-performace liquid chromatography grade methanol was purchased from Fischer & Porter Co., Warminster, Pa. All other chemicals were purchased from Sigma Chemical Co., St. Louis, Mo.

Calculations. The adenine nucleotide energy charge ratio was calculated from the formula: $EC=(ATP)+\frac{1}{2}(ADP)/(ATP)+(ADP)+(AMP)$. Extraction of adenine was calculated by taking the mean of the individual extractions derived from the formula: (Arterial adenine—coronary sinus adenine)/(arterial adenine)$\times 100$. ATP recovery rate is defined as the maximum rate of change of ATP levels during the time period specified.

Statistics. Differences between and within animal groups were evaluated by multivariate analysis (MANOVA) on the differences from baseline according to the method of S. Wallenstein, et al. in Circ. Res., Vol. 47, 1-9 (1980), the disclosure of which is incorporated by reference herein. Mean recovery time for the parameter measured is defined as the mean slope of the lines fitted to the observed points by the method of least squares. Biopsy technique was compared by linear regression analysis according to the method of least squares. Values represent mean+SE.

E. Results

Adenine, the purine base of adenosine, was not detectable in myocardial tissue ($<0.02$ nmol·mg wet $wt^{-1}$) or serum ($<1.0$ $\mu M$) collected from control animals. In treated animals the mean adenine level in myocardial tissue was $0.19\pm 0.07$ nmol·mg wet $wt^{-1}$. Mean serum levels in the ascending aorta and coronary sinus were $18.3\pm 1.3$ $\mu M$ and $11.0\pm 1.6$ $\mu M$, respectively. Calculated extraction of adenine by the myocardium was $38\pm 10\%$.

ATP levels and energy charge (EC) ratio in myocardial tissue before and for 48 hours after 20 minutes of normothermic global ischemia are presented in Table I. Data represent the values measured in septal biopsies in 16 control and treated dogs.

TABLE I

| ATP Levels (nmol · mg$^{-1}$) and EC Ratio in Treated and Control Animals* | | | | | |
|---|---|---|---|---|---|
| | Preischemic | 20 Min | 4 Hr | 24 Hr | 48 Hr |
| ATP levels+ | | | | | |
| NS (n = 7) | 5.06 ± 0.18 | 2.54 ± 0.16 | 2.33 ± 0.19 | 2.58 ± 0.26 | 2.70 ± 0.34 |
| A/R (n = 9) | 4.67 ± 0.30 | 2.08 ± 0.24 | 2.82 ± 0.26 | 4.46 ± 0.33 | 4.55 ± 0.24 |
| EC ratio§ | | | | | |
| NS (n = 7) | 0.88 ± 0.01 | 0.72 ± 0.02 | 0.75 ± 0.02 | 0.77 ± 0.02 | 0.78 ± 0.03 |
| A/R (n = 9) | 0.86 ± 0.02 | 0.67 ± 0.01 | 0.78 ± 0.02 | 0.82 ± 0.02 | 0.84 ± 0.01 |

Legend:
NS = Normal saline controls;
AR = adenine-ribose;
EC = energy: charge ratio (ATP) + ½ (ADP)/(ATP) + (ADP) + (AMP).
*Values are mean ± SE; p value is for treated versus control animals by MANOVA.
+p < 0.001.
§p = 0.008.

The data summarized in Table I demonstrate that the ATP levels decreased about 50% during ischemia in both groups but recovery of ATP in treated animals was virtually complete by 24 hours postischemia compared with 10 days in control dogs. The EC ratio also returned more rapidly in treated animals.

Of the 10 dogs that survived 7 days after ischemia, 33% of the control group and 100% of the treated group had ATP levels at or above the preischemic value in the final biopsy. In control animals the mean recovery rate for ATP levels was $0.34\pm 0.06$ nmol·mg wet $wt^{-1}$. day and the projected complete recovery time was $9.9\pm 1.4$ days. In treated dogs the mean recovery rate for ATP levels was $2.8\pm 0.59$ nmol·mg wet $wt^{-1}$. day and the projected complete recovery time was $1.2\pm 0.2$ days ($p<0.001$; treated versus controls).

These results indicate that ATP level return can be greatly enhanced despite the demands of work on the recovering myocardium. That ATP levels continue to decline during the first 4 hours of reperfusion in control dogs indicates that either the consequences of ischemia continue to produce net AMP breakdown (i.e., enzymatic degradation of AMP precursors continues at an increased rate) or the demands of cardiac function exceed the production of ATP.

De novo regeneration of ATP could be enhanced more than eightfold with adenine-ribose infusion, thus decreasing ATP recovery time from about 10 days to just over 24 hours. The faster rate of ATP recovery in treated animals during the first 4 hours of precursor infusion suggests that regeneration of ATP levels is not linear with time, and virtually complete recovery occurs even sooner than 24 hours.

EXAMPLE 2

Adenine-Ribose Infusion Duration Dependence of Post-Ischemic Recovery

The purpose of this study was to determine the required duration of adenine-ribose infusion following severe ischemia (Isc). Dogs were subjected to 20 minutes of normothermic global ischemia on cardiopulmonary bypass according to the procedures of Example 1. Following ischemia, a group of six dogs received 1 ml/min infusion of 20 mM adenine and 80 mM ribose in saline into the right atrium for 24 hr. no precursor for the next 48 hr and adenine plus ribose (A+R) for the following 24 hr. A control group of eight dogs received normal saline (NS). Left ventricular biopsies were taken pre-ischemia, at the end of ischemia, 4 hr after ischemia and daily thereafter. The biopsies were analyzed for adenine nucleotide content. The observed ATP levels set forth in Table II are umol/gm wet wt±SEM ($p* < 0.05$).

TABLE II

| | ATP Levels | | | | |
|---|---|---|---|---|---|
| Infusion | Pre-Isc | 20' Isc | 24 hr post-Isc | 72 hr post-Isc | 96 hr post-Isc |
| NS (n = 8) | 5.00 ± 0.18 | 2.50 ± 0.16 | 2.58 ± 0.29 | 3.39 ± 0.26 | 3.80 ± 0.47 |
| A +R (n = 6) | 5.56 ± 0.34 | 2.72 ± 0.66 | 3.70 ± 0.34 | 3.10 ± 0.71 | 4.17 ± 0.25 |

The data summarized in Table II confirms that enhanced recovery of ATP following ischemia occurs with adenine plus ribose infusions. Surprisingly, ATP levels again fell after cessation of A+R and later rose with restarting A+R. Similar results were obtained when A+R was discontinued after 48 hours; thereafter ATP levels also fell to NS control levels (data not shown). These results indicate that although ATP recovery following ischemia can be greatly enhanced with an adenine-ribose infusion, the consequences of ischemia persist and net ATP catabolism continues despite the recovery of ATP levels. Consequently, ATP precursor infusion must be continued, e.g. for several days, after the initial return of ATP levels to normal, in order to maintain continued tissue function recovery and to prevent the possibility of potentially serious deterioration of myocardial function.

The model systems represented in Examples 1 and 2 are designed to test the response of the intact, working heart to a global ischemic insult, a situation resembling a majority of cardiac operations. Thus, tissue perfusion according to the present invention may also be considered as an appropriate metabolic intervention in humans in clinical situations. For example, in addition to the need to immediately reverse the energetic depletion caused by open heart surgery, it is becoming a routine post-surgical to place patients whose hearts cannot maintain circulation on circulatory assistance for several hours or days. The above data suggest that adenine/ribose infusion during this procedure would also hasten energetic recovery, thereby improving survival and shortening the period of circulatory assistance.

Although the procedures of Examples 1 and 2 were directed at enhancing the energetic recovery following ischemia of the heart, the present method is expected to be applicable to any tissue or organ that has suffered ischemic insult, where reperfusion is possible. These situations include but are not limited to: stroke, organ transplant and organ transport, neonatal support, multi-organ failures, shock and trauma resulting in compromised circulation, and the like. Often, even uncomplicated general anesthesia can result in some degree of hypoxia. Therefore, the present invention provides a method whereby ischemic tissue can be treated so as to quickly regain and maintain normal ATP levels, both to improve tissue survival and to hasten general bodily recovery.

The invention has been described with respect to various specific and preferred embodiments. However, it should be understood that many variations or modifications may be made while remaining within the spirit and scope of the invention.

What is claimed is:

1. A method for reducing the recovery time of tissue function following ischemic insult comprising:
   (a) perfusing said tissue with a solution incorporating adenine and ribose in an amount effective to restore the tissue ATP level and tissue function to levels substantially equal to those present in the preischemic tissue; and
   (b) continuing said perfusion until the tissue maintains its restored function and ATP level when the perfusion is discontinued.

2. The method of claim 1 wherein said tissue is myocardial tissue.

3. The method of claim 2 wherein said ischemic insult is due to a myocardial infarction.

4. The method of claim 2 wherein said ischemic insult is due to cardiac standstill induced prior to heart surgery.

5. The method of claim 2 wherein the adenine-ribose solution is infused directly into a chamber of the heart.

6. The method of claim 1 wherein a solution of adenine and ribose is an intravenous solution is perfused.

7. The method of claim 6 wherein the solution is a normal saline solution.

* * * * *

UNITED STATES PATENT AND TRADEMARK OFFICE
CERTIFICATE OF CORRECTION

PATENT NO. : 4,605,644
DATED : August 12, 1986
INVENTOR(S) : John E. Foker

It is certified that error appears in the above-identified patent and that said Letters Patent is hereby corrected as shown below:

Column 1, line 67, for "requies", read --requires--.

Column 1, line 68, for "ia", read --is--.

Column 4, line 4, for "follwoing", read --following--.

Column 4, line 23, for "Dynograph", read --Dynagraph--.

Column 4, line 37, for "(1250", read --(250--.

Column 4, line 39, for "a", read --at--.

Column 4, line 43, for "axygos", read --azygos--.

Column 4, line 66, for "righ", read --right--.

Column 5, line 16, for "sampls", read --samples--.

Column 5, line 54, for "High-performace", read --High-performance--.

UNITED STATES PATENT AND TRADEMARK OFFICE
CERTIFICATE OF CORRECTION

PATENT NO. : 4,605,644
DATED : August 12, 1986
INVENTOR(S) : John E. Foker

It is certified that error appears in the above-identified patent and that said Letters Patent is hereby corrected as shown below:

Column 7, line 49, for "represented", read --presented--.

Column 8, line 55, for "is" (1st), read --in--.

Signed and Sealed this

Eighteenth Day of November, 1986

*Attest:*

DONALD J. QUIGG

*Attesting Officer*  *Commissioner of Patents and Trademarks*